United States Patent [19]

Aske

[11] Patent Number: 4,631,968
[45] Date of Patent: Dec. 30, 1986

[54] EFFLUENT SAMPLER

[76] Inventor: Norman L. Aske, P.O. Box 542, Westport, Oreg. 97016

[21] Appl. No.: 743,063

[22] Filed: Jun. 10, 1985

[51] Int. Cl.$^4$ .............................................. G01N 1/12
[52] U.S. Cl. .................................... 73/864.32; 73/864
[58] Field of Search ........... 73/864.32, 864.31, 864.33, 73/864.51, 864.73, 864.91, 863.41, 863.42, 863.43, 863.52, 863.53, 863.81, 864

[56] References Cited

U.S. PATENT DOCUMENTS

| | | | |
|---|---|---|---|
| 1,828,753 | 10/1931 | Spikes | 73/864.31 |
| 1,874,395 | 8/1932 | Watts | 73/864.31 |
| 2,255,369 | 9/1941 | Spaeth | 73/864.31 |
| 2,270,511 | 1/1942 | Crain | 73/864.32 |
| 2,388,801 | 11/1945 | Roetman | 73/864.32 |
| 2,958,222 | 11/1960 | Morgan | 73/864.31 |
| 3,267,737 | 8/1966 | Biebighauser | 73/864.32 |
| 3,478,596 | 11/1969 | Farrell, Jr. | 73/864.32 |
| 3,563,096 | 2/1971 | Kinkelaar | 73/864.32 |
| 3,653,265 | 4/1972 | Vallino et al. | 73/864.33 |
| 4,168,913 | 9/1979 | Kono | 366/101 |
| 4,204,431 | 5/1980 | Schulz | 73/864.31 |
| 4,314,766 | 2/1982 | Lapeyre et al. | 366/101 |
| 4,367,652 | 1/1983 | Venuso | 73/432 B |

Primary Examiner—Stewart J. Levy
Assistant Examiner—Robert Raevis
Attorney, Agent, or Firm—Klarquist, Sparkman, Campbell, Leigh & Whinston

[57] ABSTRACT

An effluent sampler includes an effluent collection container mounted accessibly within an effluent conduit and a dipper for periodically and automatically sampling the effluent stream. A collecting cup associated with the container collects a portion of the cumulative sample for an analysis thereof. The collection container is shaped to fit within an aperture of the effluent conduit and extends both inside and outside the conduit. The dipper is mounted to the container inside the conduit for protection thereof and the collecting cup associated with the container is attached outside the conduit for access to the cumulative sample. The sampler includes a compressed air system for clearing the dipper and a second compressed air system for intermixing the cumulative sample therewithin. For collecting effluent, a collecting head is attached to the dipper.

9 Claims, 5 Drawing Figures

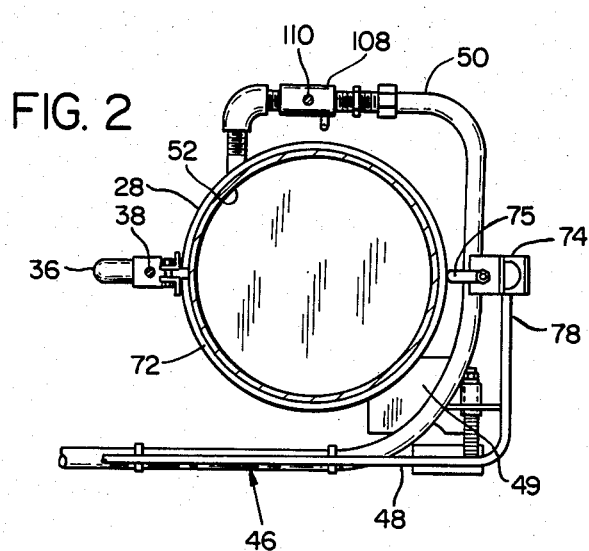
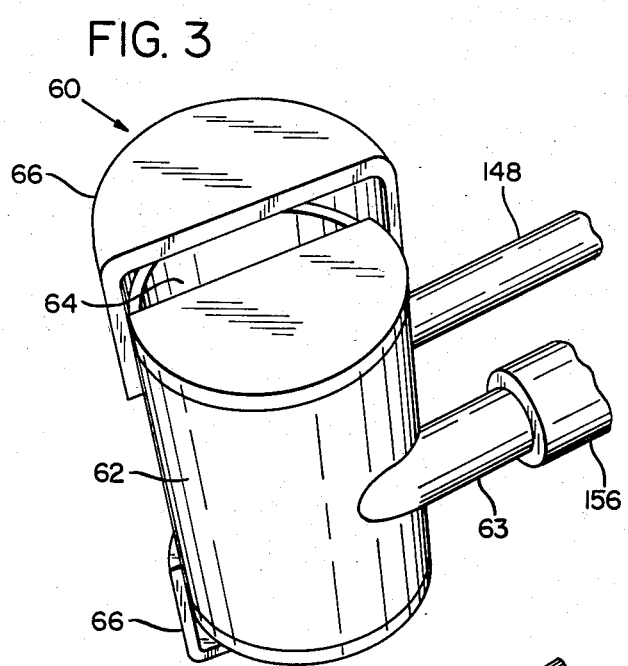
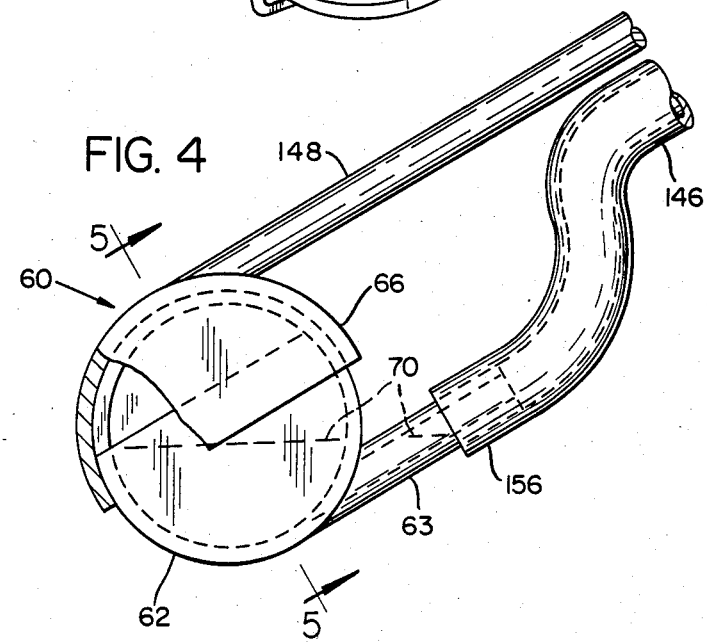
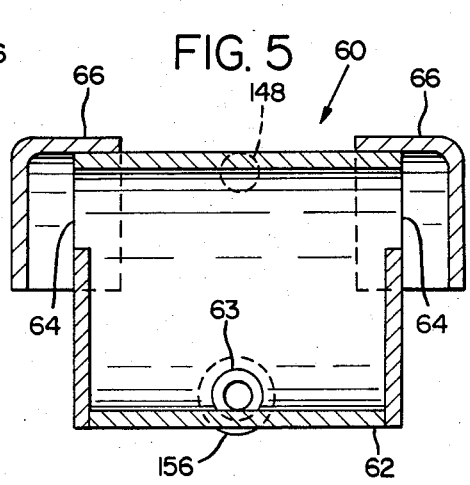

EFFLUENT SAMPLER

BACKGROUND OF THE INVENTION

This invention generally relates to effluent samplers and more particularly, to an effluent sampler of improved efficiency, accuracy and structural design.

Effluent samplers are used to monitor the composition of effluent being discharged from a factory or mill. A sampler selectaby removes a sample of effluent from an effluent stream and retains samples for subsequent chemical analysis. By analyzing these samples, it can be determined whether manufacturing processes within the facility are working properly or whether discharges of excessive wastes are occurring.

Representative effluent samplers are disclosed in U.S. Pat. Nos. 2,270,511 to Crain and 2,958,222 to Morgan. In Crain, the sampler rests atop the effluent conduit adjacent to an opening for access to an effluent stream. An arm having a sample cup is pivotally connected to a motor drive. At the bottom of the cut is a valve to permit entry of effluent materials. In operation, the motor drive lowers the arm and cup from above the conduit through the opening and into the stream. Fluid collects through the valve in the bottom of the cup, and the arm and the cup are then raised from the stream and the sample is deposited in a storage container.

Morgan discloses a sampler mounted above the effluent stream. The sample is gathered by a pivoting arm with an opening at one end for retention of a sample. The arm pivots into the stream flow and then rises to pour the sample into a receptacle. To control admission of effluent into the arm, the opening is selectively opened or closed by a gate.

Other samplers are shown in U.S. Pat. Nos. 3,563,096 to Kinkelaar, 3,267,737 to Biebighauser, and 2,388,801 to Roetman. Kinkelaar shows a sampler that mounts above the effluent conduit. It samples the effluent with a sample container suspended from a motor unit. The container is lowered into the effluent stream and the sample is collected. The container is then raised and inverted to discharge the sample into a receptacle.

Biebighauser discloses a sampler that is affixed to a surface within the effluent conduit. It samples the effluent stram with a collecting cup mounted on a reciprocating arm. The reciprocating arm extends into the effluent stream to collect the sample and twists as it retracts to pour the sample into a receptacle.

In Roetman, the sampler is mounted above the effluent stream within a collection flume. It includes a catch basin to which a dipper is pivotally connected. The dipper dips downward into the stram to obtain a sample and then pivots uward to pour the sample into the catch basin.

The primary drawback of these samplers and others in the prior art is the inconvenience of use. Effluent streams generally flow in a conduit through a facility. Effluent samplers that must be mounted within the conduit are largely inaccessible for recovering their samples. Those that are mounted above the conduit, on the other hand, often present an obstruction in the facility.

Another drawback of the prior art is its failure to furnish a representative sample of the discharged effluent. The samples that are collected in the receptacle contain particulate matter and liquids of varying densities that filter into different layers within the container. The sample recovered from the container may not reflect a true mix of the effluent actually discharged and will likely include less particulate matter and lighter fluids.

The prior art also lacks means for easily cleaning an effluent sampler. If not removed from the sampler, particulate matter can deposit within an arm or dipper and eventually block flow of effluent to the collection point or may later dissolve to contaminate future samples.

SUMMARY OF THE INVENTION

It is an object of the invention to provide an improved effluent sampler that may be mounted accessibly within an effluent conduit.

It is another object of the invention to provide a sampler that collects periodic samples of effluent and intermixes them into a cumulative sample which accurately reflects the composition of the effluent being discharged.

It is yet another object of the invention to provide an effluent sampler that may be easily cleaned.

To achieve these objects, an effluent sampler according to the invention includes an effluent collection container having mounting means thereon for mounting the container accessibly within the conduit. Sampling means are mounted to the container for automatically sampling the effluent stream periodically and depositing the samples within the container to form a cumulative sample. Collecting means such as an extendable collecting cup is provided for collecting a portion of the cumulative sample for analysis.

In the preferred embodiment, the container is shaped to fit within an aperture of an effluent conduit wall and is mounted to extend both inside and outside of the conduit. The sampling means is mounted to the container inside the conduit for protection thereof and the collecting means is provided outside the conduit for ease of access to the cumulative sample. The sampling means may comprise a dipper pivotally mounted to the container. The dipper dips into the effluent stream to collect the sample and then rises to deposit the sample within the container. Vent means, such as a compressed air source, may be provided to clear the sample of effluent obstruction with compressed air.

In one aspect of the invention, the dipper may include a collecting head means for trapping effluent therein. The head includes a collecting trough and a guide for directing effluent into the trough and from there into the dipper.

To provide a representative sample of the effluent, agitating means may be provided to intermix the cumulative sample. The agitating means comprises a compressed air source for directing compressed air into the cumulative sample through a mixer tube.

The effluent sampler of the present invention overcomes the drawbacks of previous samplers. It mounts within an existing manhole of an effluent conduit, with the dipper and associated operating mechanism protected within the conduit and the cumulative sample readily accessible from above the conduit by an extendable cup. It provides a representative sample of the effluent collected over a predetermined period. It is also self-cleaning to lower maintenance and improve operation.

The foregoing and other objects, features, and advantages of the invention will become more apparent from the following detailed description of a preferred embodiment which proceeds with reference to the accompanying drawings.

BRIEF DESCRIPTION OF THE DRAWINGS

FIG. 2 is a cross-sectional view of FIG. 1 taken along line 2—2;

FIG. 3 is a perspective view of a dipper head;

FIG. 4 is a cross-sectional view of the dipper head; and

FIG. 5 is a sectional view taken along line 5—5 of FIG. 4.

DETAILED DESCRIPTION

Figure 1:
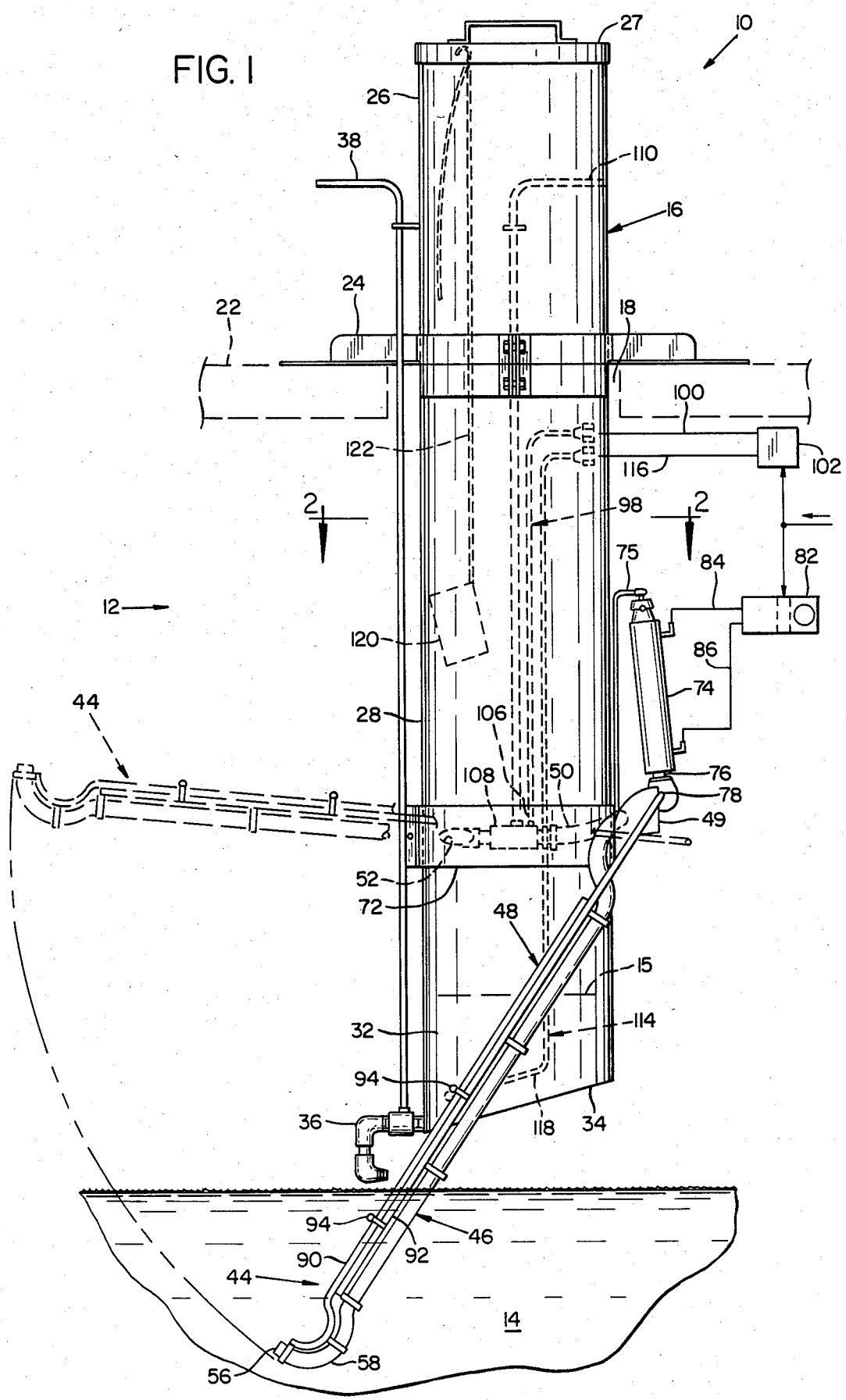
FIG. 1 is an elevational view of an effluent sampler according to the invention.

An effluent sampler 10 according to the invention is shown in FIG. 1. The sampler is mounted vertically within an underlying horizontal effluent conduit 12 to periodically sample the effluent of a stream 14 flowing through the conduit. The effluent may be the discharge from a manufacturing process and is monitored to determine its composition. The periodic sample collected is deposited within sampler 10 to form a cumulative sample 15 that reflects the effluent's composition for a predetermined time, such as a day's operation. A representative portion of the cumulative sample is removed periodically from sampler 10 for chemical analysis of the effluent discharged during that time.

Sampler 10 includes elongated cylindrical collection container 16 made of a strong, lightweight material such as stainless steel and mounted accessibly within conduit 12. In FIG. 1, container 16 fits within an aperture such as a manhole 18 in conduit wall 22. Container 16 is mounted in manhole 18 by adjustable wings 24 banded to the container and extending beyond manhole 18 to abut wall 22 for support.

As shown in FIG. 1, container 16 extends both inside and outside conduit 12. An upper portion 26 of the container extends above conduit 12 to provide ready access to the contents thereof. Removably mounted to upper portion 26 is a lid 27 that rests atop container 16 to protect cumulative sample 15 from outside contamination. A lower portion 28 of container 16 extends within conduit 12 toward effluent stream 14. The length of lower portion 28 is determined by the depth of conduit 12. It extends sufficiently into the conduit to place it adjacent the stream flow. Within lower portion 28, a catch basin 32 is disposed to receive periodic samples and form cumulative sample 15. Catch basin 32 includes a funneled bottom 34 and a drain valve 36 at the nadir of bottom 34 for draining cumulative sample 15 into stream 14 after a representative portion has been collected from the basin. Drain valve 36 is operated by a control rod 38 extending from the valve through manhole 18 and above conduit 12, where the rod is readily accessible.

To gather samples from effluent stream 14, a sample means such as a dipper 44 is pivotally mounted to lower portion 28 of collection container 16. Dipper 44 comprises an extendable, flexible hose 46 supported by a coextensive dipper rod 48 that is pivotally mounted to container 16, as seen in FIG. 2. Upper end 50 of hose 46 connects to catch basin 32 through an inlet 52 of container 16. Hose 46 wraps around collection container 16 and outward along dipper rod 48. A lower, collecting end 56 of hose 46 bends to form a catch 58. By pivoting rod 48 on a bracket 49 attached to container 16, hose 46 can be dipped to lower end 56 into stream 14 to collect a sample and can be raised to pour the sample into catch basin 32.

Another embodiment of the sample means is shown in FIGS. 3-5. A collecting head 60 connects to a dipper rod 148 and a collecting end 156 of a hose 146. Head 60 includes a cylindrical collecting trough 62 mounted with its lengthwise axis normal to hose 146. An inlet pipe 63 extends from trough 62 into collecting end 156 to complete the connection. Effluent enters trough 62 through semicircular apertures 64 on each end of the trough. To direct effluent therein, guide ears 66 overlap each end of trough 62 and extend over semicircular apertures 64. Guide ears 66 form an inlet into trough 62 to intercept flowing effluent and channel it into the trough, as shown in FIG. 4. When dipper 44 is raised, a collected sample 70 is retained by head 60 and pours into catch basin 32 through hose 146. Dipper 44 picks up larger samples as the effluent level increases above head 60.

Dipper 44 is pivotally mounted to collector container 16 on a metal support band 72 welded to bracket 49 and also supports actuating vertical air cylinder 74 on a bracket 75. Referring to FIGS. 1 and 2, a cylinder rod 76 extends from the bottom of cylinder 74 and connects to an upper end 78 of dipper rod 48 to pivot dipper 44. Compressed air from a source (not shown) is released through a timer-controlled solenoid valve system 82 and directed through air lines 84 and 86 to cylinder 74. To raise dipper 44, compressed air enters cylinder 74 through line 84 and withdrawn through line 86 to extend cylinder rod 76. To lower dipper 44, valve system 82 directs air into line 86 and out of line 84, thereby retracting cylinder rod 76.

Because the level of the stream flow may vary, the length of dipper 44 may be adjusted by incorporating an extension rod 90 into dipper 44. Referring to FIG. 1, an extension rod 90 is adjacent lower end 92 of dipper rod 48 and attached thereto by adjustable thumb screws 94. By extending and retracting hose 46 and extension rod 90, dipper 44 can be lengthened or shortened as required.

Cleaning effluent obstruction from hose 46 is accomplished by venting means such as a first compressed air system connected to the compressed air source. Referring to FIGS. 1 and 2, the system comprises an air tube 98 receiving compressed air through a line 100 from a control valve 102. Lower end 106 of tube 98 is joined to a two-way valve 108 connecting upper end 50 of hose 46 to container inlet 52. Valve 108 is controlled by a second control rod 110 extending from valve 108 up through manhole 18 and above conduit wall 22 for ready access. By turning control rod 110 in one direction, valve 108 is shut off to foreclose entry to inlet 52. Compressed air can thus be blown back through hose 46 away from inlet 52 and out collecting end 56.

Effluent that does enter catch basin 32 from dipper 44 is intermixed by agitating means to provide a representative sample of effluent collected over a predetermined period. Referring to FIG. 1, a second compressed air system connected to the compressed air source directs compressed air into a vertical mixing tube 114 through line 116 from control valve 102. Tube 114 extends lengthwise within collection container 16 down into catch basin 32, with its lower end 118 adjacent to funneled bottom 34. Compressed air is periodically released manually or automatically through control valve 102 and tube 114 to bubble up through cumulative sample 15 and thereby intermix different layers of effluent within catch basin 32.

A representative portion of intermixed cumulative sample 15 is collected by an extendable collecting cup 120. Cup 120 is lowered from upper portion 26 of collection container 16 into catch basin 32 to collect the sample. To retain cup 120, it is attached to a retaining chain 122 mounted to collection container 16. The collected portion of cumulative sample 15 is then chemically analyzed to determine the composition of the effluent discharged during that period.

In operation, sampler 10 is used to collect a representative sample of effluent discharge over a predetermined time. Dipper 44 is under control of timer-controlled solenoid valve 82 to automatically and periodically dip into effluent stream 14 and collect a periodic sample for deposit into catch basin 32. The sampling rate, of course, may be varied as required by adjusting solenoid valve 102. The periodic samples form cumulative sample 15, which is intermixed by air from mixing tube 114. A representative sample of cumulative sampler 15 is collected from catch basin 32 by collecting cup 120 for analysis of the effluent's makeup. The remainder of cumulative sample 15 is then discharged from catch basin 32 by opening drain valve 36 with control rod 38. After the sample is taken, hose 46 may then be cleaned by directing compressed air through air tube 98 and back through hose 46.

Having illustrated and described the principles of the invention in a preferred embodiment, it should be apparent to those skilled in the art that the invention can be modified in arrangement and detail without departing from such principles. I claim all modifications coming within the spirit and scope of the following claims.

I claim:

1. An apparatus for sampling an effluent stream flowing within a conduit having an aperture within a wall of the conduit, comprising:
    an effluent collection container mounted accessibly within the conduit aperture, the container having an upper portion above the conduit wall to permit access within the container and a lower portion below the conduit wall;
    sampling means mounted to the lower portion of the container for sampling the effluent stream periodically and depositing the periodic samples within the container to form a cumulative sample for a predetermined period; and
    collecting means associated with the container for collecting a portion of the cumulative sample and delivering the portion to the upper portion of the container for analysis thereof.

2. The apparatus of claim 1 in which the apparatus further includes a first compressed air source for clearing the sampling means of effluent obstruction therein.

3. The apparatus of claim 2 in which the sampling means comprises a dipper pivotally mounted to the container to dip into the effluent stream for a sample and to rise to deposit the sample within the container, the dipper cleared of effluent after each dip by the compressed air source.

4. The apparatus of claim 3 in which the length of the dipper is adjustable to corresposed to the depth of the effluent stream.

5. The apparatus of claim 3 in which the dipper includes a collecting head means for trapping effluent therein.

6. The apparatus of claim 5 in which the collecting head means comprises a collecting trough and a guide for directing effluent into the trough.

7. The apparatus of claim 1 further comprising a compressed air source for automatically and periodically directing air into the container for intermixing the cumulative sample therewithin, the source thereby providing a representative sample of the effluent deposited within the container during the predetermined period for collection by the collecting means.

8. The apparatus of claim 1 in which the container includes an outlet for releasing the cumulative sample into the effluent stream to clear the container for a second cumulative sample, and means to close the outlet when the container is cleared.

9. An apparatus for sampling an effluent stream flowing within a conduit having an aperture within a wall of the conduit, comprising:
    a cylindrical effluent collection container having wings thereon for mounting the container within the conduit aperture above the effluent stream, the container having an upper portion with an opening in the portion above the conduit and a lower portion below the conduit wall;
    a dipper pivotally mounted to the lower portion of the container to periodically dip into the stream for a sample and to deposit the periodic sample within the container to form a cumulative sample;
    first compressed air means for directing compressed air through the dipper periodically to clean it of effluent obstruction therein;
    second compressed air means for directing compressed air into the cumulative sample periodically to intermix the cumulative sample, thereby providing a representative sample of the effluent deposited within the container; and
    collecting means within the container for collecting a portion of the cumulative sample, the collecting means delivering the portion of the cumulative sample to the container opening within the upper portion of the container for analysis thereof.

* * * * *